(12) United States Patent
Kim

(10) Patent No.: US 8,604,239 B2
(45) Date of Patent: Dec. 10, 2013

(54) DIETHYLENE TRICARBAMIDE AND DIETHYLENE TRICARBAMIDE-FORMALDEHYDE CONDENSATION RESINS

(75) Inventor: Moon Kim, Starkville, MS (US)

(73) Assignee: Mississippi State University Research and Technology Corporation, Mississippi State, MS (US)

( * ) Notice: Subject to any disclaimer, the term of this patent is extended or adjusted under 35 U.S.C. 154(b) by 0 days.

(21) Appl. No.: 13/506,567

(22) Filed: Apr. 27, 2012

(65) Prior Publication Data

US 2012/0316270 A1    Dec. 13, 2012

Related U.S. Application Data

(60) Division of application No. 12/653,276, filed on Dec. 10, 2009, now abandoned, which is a continuation-in-part of application No. 12/001,056, filed on Dec. 7, 2007, now abandoned.

(51) Int. Cl.
| | | |
|---|---|---|
| *C07C 269/02* | (2006.01) | |
| *C07C 273/02* | (2006.01) | |
| *C07C 273/08* | (2006.01) | |

(52) U.S. Cl.
USPC .................. 564/61; 564/32; 564/58; 564/59; 525/418

(58) Field of Classification Search
USPC ........................... 564/32, 58, 59, 61; 525/418
See application file for complete search history.

(56) References Cited

U.S. PATENT DOCUMENTS 3,271,335 A * 9/1966 Bostian et al. .................. 524/14

OTHER PUBLICATIONS

Bertoniere, J. Appl. Polym. Sci. 23, 2567-2577 (1979).*

* cited by examiner

*Primary Examiner* — Robert C Boyle
(74) *Attorney, Agent, or Firm* — Lawrence Arthur Schemmel

(57) ABSTRACT

The present invention provides manufacturing of and the use of novel diethylene tricarbamide and its condensation reaction products formed by reacting with formaldehyde as wood composite binder resins and in other applications. These resins have thermosetting capabilities and therefore usefulness as binders for wood and other materials with superior resin properties of low cost, colorlessness, exceptionally good binding, and fast curing characteristics, as well as very low formaldehyde emissions. The synthesized novel starting material for the thermosetting resins of the present invention is diethylene tricarbamide.

17 Claims, 2 Drawing Sheets

DIETHYLENE TRICARBAMIDE AND DIETHYLENE TRICARBAMIDE-FORMALDEHYDE CONDENSATION RESINS

CROSS-REFERENCE TO RELATED APPLICATIONS

This application is a divisional application of continuation-in-part application Ser. No. 12/653,276, filed Dec. 10, 2009 now abandoned, which was a continuation-in-part of U.S. patent application Ser. No. 12/001,056, filed Dec. 7, 2007 now abandoned, the entire contents of each of which are incorporated herein by reference.

STATEMENT OF GOVERNMENT SUPPORT

This invention was made with government support under grant 2002-34158-11926 awarded by the U.S. Department of Agriculture WUR and 0171146 awarded by the Cooperative State Research, Education, and Extension Service, USDA. The government may have certain rights in the invention.

FIELD OF THE INVENTION

The present invention relates to the field of wood composite binder resins and other areas of application. In particular, the present invention relates to manufacturing and using novel diethylene tricarbamide and its condensation reaction products formed by reacting with formaldehyde, which have thermosetting capabilities and usefulness as binders for wood and other materials as well as in other applications.

BACKGROUND OF THE INVENTION

Urea-formaldehyde (UF) resin adhesives are commonly used to produce wood composite products such as particleboard, medium-density fiberboard, and hardwood plywood panels. These UF resins are considered good binders in these applications due to high physical strength properties, fast curing times, and high cost-efficiency. Two major drawbacks to UF resin-based systems, however, are the limited strength durability of the resulting composite products as well as the emission of formaldehyde. Formaldehyde emissions are of particular concern when using UF resin-bonded boards for interior purposes such as sub-flooring, shelving, cabinets, and furniture. Air concentrations of formaldehyde above 0.1 parts per million (ppm) are associated with acute health effects, including watery eyes, burning sensations in the eyes, nose and throat, nausea, coughing, chest tightness, wheezing, skin rashes, headaches, fatigue, asthma, and other irritating effects. Formaldehyde has been shown to be cancer-causing in laboratory animals, although there is limited evidence of cancer-causing effects in humans. Nevertheless, it is classified as a "probable human carcinogen" by the United States Environmental Protection Agency (EPA) and the National Institute for Occupational Safety and Health.

Both the formaldehyde emission problem and the durability issues of UF resin-bonded wood products are linked to the underlying chemistry of the UF resin system. During synthesis of resin, hydroxymethyl groups are formed from the reaction of formaldehyde (F) and urea (U) as functional groups needed for the subsequent polymerization and curing processes. However, the reverse reaction of hydroxymethyl group formation also occurs during synthesis and subsequent curing processes to generate back some free formaldehyde, which is later emitted into the environment. The extent of the reverse reaction is generally proportional to the F/U mole ratio used in resin synthesis and is relatively small in comparison to the forward reaction, but still persists to the current low F/U molar ratio for resins of about 1.15 (Myers, G. E. Holzforschung 44:117-126 (1990); Forest Products Journal 34:35-41 (1984). This is the underlying mechanism for the formaldehyde emission phenomena of UF resin-bonded wood composite boards. This low F/U mole ratio of resin needed for lower emission, on the other hand, translates into a functionality value of about 2.3 formaldehyde molecules per urea molecule in current UF resins. Polymer molecular theory on the formaldehyde-based thermosetting resins indicates that the base monomer (for example, urea) needs to have a functionality of at least 3.0 or higher to make the resin polymers grow to a three-dimensional, fully cross-linked state (Flory, P. J. *Polymer Chemistry*, Cornell University Press, Ithaca, N.Y. (1953) p. 79.). Since the urea functionality in current UF resins is significantly lower than the theoretical value, a full cross-linking does not occur and the cured resin binders will result in limited strength durability of boards. The formaldehyde emission problem still persists at the current F/U mole ratio values of resin. Currently, UF resin formulation (mostly lowering of F/U mole ratio) and scavenger parameters have been pushed to limits for reduction of formaldehyde emission from boards, but significant further formaldehyde emission reductions are desired. From the above theoretical consideration, such a reduction in formaldehyde emission level for UF resin-bonded boards seems to require a significant redesigning of the starting molecule toward materials having higher functionality than urea. There accordingly remains a need in the art for interior-grade wood composite binder resins for improved starting materials as well as their formaldehyde condensation products that give superior resin properties of low cost, colorlessness, exceptionally good binding, and fast curing characteristics, as well as very low formaldehyde emissions. The present invention provides such advantages.

SUMMARY OF THE INVENTION

It is an object of the present invention to provide manufacturing of and the use of novel diethylene tricarbamide and its condensation reaction products formed by reacting with formaldehyde as wood composite binder resins and in other applications.

The newly-designed and synthesized novel starting material for the thermosetting resins of the present invention is diethylene tricarbamide. The diethylene tricarbamide is reacted with formaldehyde at elevated temperatures in weak alkaline and then optionally in weak acidic pH, or only in weak acidic pH, to result in thermosetting resins useful in many applications, including binders for wood composite boards such as particleboard, medium density fiberboard, hardwood plywood, and others with improved board strengths while having very low potentials of formaldehyde emission. Another advantage of the resin materials of the present invention is the inter-miscibility of variously synthesized carbamide-formaldehyde and urea-formaldehyde resins and also with urea or melamine in any proportions to take advantages of lower cost or lower formaldehyde emission properties.

The thermosetting resin materials of the present invention with an acid-generating latent catalyst and with or without other filler additive materials are applied on substrates and cured at elevated temperatures of about 120° C.-300° C. until hardened. The cured resin materials show good stability at the curing temperatures and also good durability and strength after cooling to room temperature to be useful as adhesives, impregnating matrix binders, treatment chemicals, and other areas where high strength/weight ratios are needed. The handling and curing properties of resins of the present invention are especially suited to industrial thermosetting processes including manufacturing wood composite boards such as particleboard, medium density fiberboard, hardwood and softwood plywood, oriented strand board, strawboard, and the like and treatments of paper, cotton textiles, leather, cardboard, felt, sand mold, and the like. The resins of this disclosure can be useful as binders for non-woven materials such as paper, cotton, leather, cardboard, and other felt products to improve the wet and dry strengths and also can be useful as binders for sand molds in the metal casting industry. The diethylene tricarbamide and diethylene tricarbamide-formaldehyde condensation products of the present invention are quite unique and novel and likely useful in many industrial processes. The diethylene tricarbamide was for the first time synthesized and found to be useful as starting materials of thermosetting resins and may also be used in areas other than manufacturing of formaldehyde condensation products. It is to be understood that changes and variations may be made without departing from the spirit and scope of the invention as defined in the appended claims.

With the foregoing and other objects, features, and advantages of the present invention that will become apparent hereinafter, the nature of the invention may be more clearly understood by reference to the following detailed description of the preferred embodiments of the invention and to the appended claims.

BRIEF DESCRIPTION OF THE DRAWINGS

These drawings accompany the detailed description of the invention and are intended to illustrate further the invention and its advantages.

DETAILED DESCRIPTION OF THE INVENTION

Figure 1:
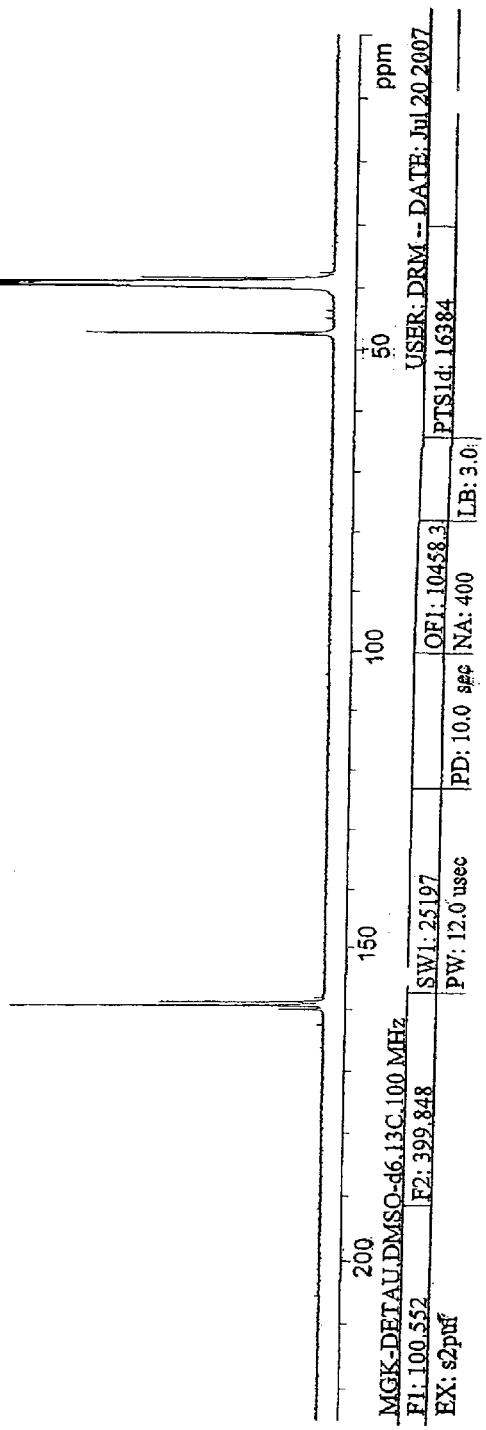
FIG. 1 is a graphical illustration of a typical $^{13}$C NMR spectrum obtained in dimethyl sulfoxide as solvent for "diethylene tricarbamide" synthesized in synthesis Method 1 and 2.

The present invention provides for the manufacturing of and the use of novel diethylene tricarbamide and its condensation reaction products formed by reacting with formaldehyde as wood composite binder resins and in other applications. Additional objectives and advantages of the present invention are to provide products with exceptional thermosetting capabilities and usefulness as binders for wood and other materials. It will be understood by those skilled in the art that the present invention is not limited in its application to the details of the arrangements described herein since it is capable of other embodiments and modifications. Moreover, the terminology used herein is for the purpose of such description and not of limitation.

Synthesis Methods of Diethylene Tricarbamide

Diethylenetriamine ($NH_2$—$CH_2CH_2$—NH—$CH_2CH_2$—$NH_2$)), a known polyamine compound, was reacted either with urea (Method 1) or sodium cyanate (Method 2) to obtain diethylene tricarbamide in good yields. The procedures were adapted from methods known for simple monoamines. The synthesized polycarbamide was found to be very stable under ordinary conditions as well as in heating or mild acid or base treatments.

Method 1—In this procedure, the polyamine is reacted with a slight molar excess of urea in the presence of water as solvent to obtain the diethylene tricarbamide by splitting off ammonia:

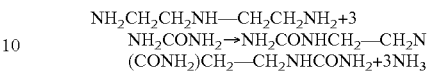

This method is well known for simple amines (Organic Synthesis 3, 95 (1923)). In this disclosure, diethylenetriamine is reacted with urea as follows: In a 500 mL three-neck flask equipped with a stirrer, condenser, and thermometer, 90.0 grams of diethylenetriamine (0.87 mole) were dissolved in 2.5 L of water and then added 210.0 grams of urea (3.5 moles). Then, the stirred reaction mixture was heated to 100-104° C. over a period of 30 min and allowed to react for an hour, followed by allowing a slow distillation of water containing ammonia for three hours. Finally, the distillation was continued under water-vacuum for 30 min and then the remaining solution was poured off on to a pan and allowed to cool to room temperature. The separated colorless precipitates were collected as crude diethylene tricarbamide (121 grams), which can be purified by dissolving or making slurry in water at elevated temperatures followed by cooling and filtration and drying. The analysis results are recorded in Table 1. Furthermore, in this method, the reaction medium (solvent) of choice for the reaction can also be varied such as pyridine, formamide, dimethyl formamide, dimethyl sulfoxide, n-butanol, n-pentanol, cyclohexanol, ethylene glycol, and glycerine, etc. and mixtures of these solvents together and with water. The purification solvents of choice are the same solvents used in the reaction as well as various low molecular weight alcohols such as methanol, ethanol, and n-propanol. These variations in reaction and purification solvents afford only the reaction yield variations and convenience of operations. The reaction temperature can be as high as 180° C. or the boiling point of the reaction mixture.

Method 2—In this procedure, the polyamine is reacted with sodium cyanate (NaOCN) in the presence of an acid (HX) and water as a solvent to obtain the diethylene tricarbamide by splitting off sodium salt of the acid:

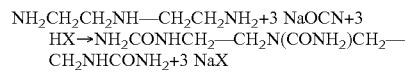

This method is well known for monoamines (Vogel, A. I. Practical Organic Chemistry 3$^{rd}$ Ed., Longman, London (1972), p. 644). In this disclosure, diethylenetriamine is reacted with sodium cyanate as follows: In a 500 mL three-neck flask equipped with a stirrer, condenser, and thermometer, 104 grams of diethylenetriamine (1.0 mole) were dissolved in 500 mL of water and then added 142 grams of sulfuric acid (1.5 moles) with external cooling to about 65° C. Then, to the stirred, warm reaction mixture, 215 grams of sodium cyanate (3.3 moles) were added over a period of 30 min, followed by reacting an additional hour at the same temperature. Finally, the reaction mixture were cooled to room temperature and the separated colorless precipitates collected as crude diethylene tricarbamide (162 grams), which was purified by dissolving in water at elevated temperatures followed by cooling and filtration and drying. The acid (HX) can be any inorganic or organic acid such as sulfuric, phosphoric, nitric, hydrochloric, formic, acetic, and oxalic acid.

The synthesized diethylene tricarbamide showed a melting point of 217-219° C. and correctly analyzed by $^{13}$C NMR as shown in FIG. 1 and infrared spectra and also by carbon, hydrogen, and nitrogen elemental analysis as shown in Table 1.

TABLE 1

| Starting polyamine Structure/Name | Yield (%) | Synthesized carbamide Structure/Name | $^{13}$C NMR chemical shift (ppm) | Melting Points ° C. | Major ir Peaks cm$^{-1}$ | Carbon, nitrogen, Hydrogen analysis (%): Theory/Observed | | |
|---|---|---|---|---|---|---|---|---|
| | | | | | | C | H | N |
| NH$_2$CH$_2$CH$_2$NH— CH$_2$CH$_2$NH$_2$ Diethylenetriamine | 60%~93% | NH$_2$CONHCH$_2$— CH$_2$N(CONH$_2$)CH$_2$— CH$_2$NHCONH$_2$ Diethylene tricarbamide | 159.26:38.53 47.44:158.70:47.44 38.53:159.26 | 217-219 | 3420; 3370; 3220 2950; 1660; 1560 | 36.20/35.47 | 6.95/6.98 | 36.19/35.62 |

In conclusion, the synthesized diethylene tricarbamide of the present invention shown in Table 1 was a new compound synthesized for the first time by the inventor and the chemical structures are fully characterized through the synthetic procedures and the various analytical results. Diethylene tricarbamide is composed of organic carbon-chain backbones and has three amide functional groups in a molecule for reaction with formaldehyde. Comparing to urea's two carbamide functional groups in a molecule, the greater number of functionality of the starting materials of the present invention have manifested the novelty in reaction with formaldehyde and the reaction products' resin properties and cured polymers' usefulness as adhesives and other applications as demonstrated in the Examples below.

Synthesis Methods of Diethylene Tricarbamide-Formaldehyde (DTC-F) Resins with no Poly-Condensation Step Synthesis of the thermosetting resins of the present invention was accomplished by reacting synthesized diethylene tricarbamide with formaldehyde, resulting in useful thermosetting resins. In the typical resin synthesis procedure, an appropriate amount of formaldehyde solution is charged into a stirred reactor equipped with a thermometer and condenser along with water to keep the resin solids level to the common 50%-60% range. The pH of the formaldehyde solution is then adjusted to 5.5-9.0 and heating is applied to heat the reactor to about 40° C.-90° C. Then, the solid polycarbamide is added in small portions over a period of 20-30 min and heating is continued to maintain the reaction mixture at 60° C.-106° C. for 15 min or longer until the reaction mixture becomes clear. The condensation reaction is continued for 0.5-2 hours at the same temperature with the pH of the reaction mixture being maintained at 6-10 for completion of the condensation reaction. The concentration of formaldehyde and polycarbamide in the initial reaction mixture should be between 10% and 90%. The mole ratio of formaldehyde to diethylene tricarbamide in the reaction should be between 0.1 and 1.5 moles of formaldehyde per each carbamide group with the preferred ratio being 0.2 to 1.2 moles. The formaldehyde can be in any form, commonly 37% to 60% aqueous solutions or solid paraformaldehyde, as long as the overall levels of reactants are maintained by using an appropriate amount of water. However, the 50% formaldehyde solution is commonly used in the thermosetting resin manufacturing industry. The temperature of the reaction may be varied from 30° C. to the boiling point of the reaction mixture, which may go as high as 106° C. under normal atmospheric pressure. After completion of the reaction described above, the product is cooled to room temperature and can be used directly with or without some additional acidic catalysts. When the reaction products need to be stored or transported, the pH must be adjusted to 6.0-9.0 by adding a suitable alkaline material such as ammonia, sodium or potassium hydroxide or carbonate. Analyses of the polycarbamide-formaldehyde condensation reaction products using $^{13}$C NMR spectroscopy (FIG. 2) indicated the almost quantitative formation of hydroxymethyl groups bonded to the carbamide groups in accord with the chemistry known for urea in literature (Kim, M. G. J. Polymer Science, Part A: *Polymer Chemistry*, 37: 995-1007 (1999)).

Syntheses of Oligomeric Carbamide-Formaldehyde (DTC-F) Resins by Further Condensation in Acidic pH For preparation of higher molecular weight oligomeric polycarbamide-formaldehyde resin products, the condensation reaction product described above is acidified by adding a dilute solution of a strong acid such as sulfuric acid or hydrochloric acid (~8%) to pH 5.0-6.9 and then reacted at about 30° C.-105° C. The optimum temperature and optimum pH and the reaction time depend on the target extent of polymerization. During the condensation reaction, the resin-rich phase can start to separate from the water-rich phase. Most often, the condensation reaction is ended before such a separation occurs or, if more advanced resin is needed, water is distilled off from the separated resin mixtures to obtain homogeneous reaction products. After the target extent of poly-condensation is attained by monitoring the viscosity or other variables, the reaction is ended by adjusting the reaction mixture to pH 6.0-9.0 by adding 0.8% sodium hydroxide solution or other dilute bases and cooling to room temperature. The analyses of these advanced resins using $^{13}$C NMR spectroscopy showed various extents of formation of methylene and methylene-ether groups between amide groups from some of the hydroxymethyl groups formed in the first alkaline step. The $^{13}$C NMR spectrum in FIG. 2 for the resin of Example 1 shows the carbon groups appearing over the chemical shift range of about 47~160 ppm. Overall, the resin synthesis reaction patterns in the alkaline and acidic pH and the $^{13}$C NMR results all agree with the chemical principles of typical thermosetting resins such as urea-formaldehyde resins, as illustrated below:

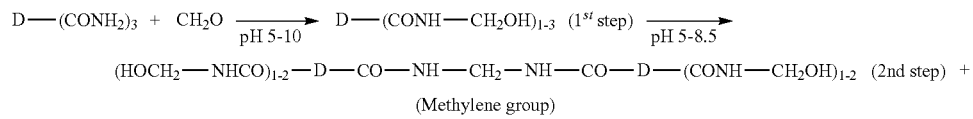

(Methylene group)

-continued

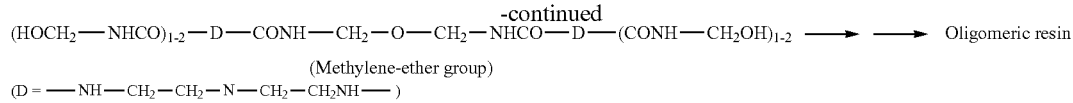

(Methylene-ether group)
(D = —NH—CH$_2$—CH$_2$—N—CH$_2$—CH$_2$NH—)

Syntheses of Copolymer Resins of Diethylene Tricarbamide-Formaldehyde (DTC-F) Resins with Urea or Urea-Formaldehyde Resins The diethylene tricarbamide and its formaldehyde reaction products (DTC-F) of the present invention are very well miscible with and also can react to form co-polymers with urea or urea-formaldehyde (UF) resins under the common resin synthesis and curing conditions. Many different mixing and reacting procedures can be used: urea or UF resins or UF concentrates can be added to finished DTC-F resins or in the beginning of the resin synthesis procedures. Also, minor amounts of DTC-F resins can be added to finished UF resins. For lowering the resin cost and various other reasons, these copolymer resins can be advantageous in various applications.

Other Handling and Use Properties of Diethylene Tricarbamide-Formaldehyde (DTC-F) Resins of the Present Invention The cooled, neutralized resins of the present invention can be stored or transported to the point of use. An acid catalyst is needed in application for accelerating the cure of resins when used as adhesives and laminates and the like. Ammonium or any organic amine salts of strong acids such as sulfuric acid, hydrochloric acid, nitric acid, phosphoric acid, toluene sulfonic acid, formic acid and any of these acids may be used in an amount of 0.1%-6.0% based on the weights of resin solids. In the case of bonding wood, no catalyst may be necessary due to the acids in the wood. The catalysts start the polycondensation reaction of hydroxymethyl groups and external heating accelerates the curing reaction further. The hydroxymethyl groups react further with each other and also with the other carbamide groups, so that the polymer molecules grow three-dimensionally and finally cross-link to form solid thermoset polymers of the adhesives, matrices, and the like.

DTC-F resins are dispersible in water and therefore can be diluted by adding water or condensed by distillation of water or spray-dried to solid particles before application. In addition to curing catalysts, other agents can be added to the resins for other purposes: various ionic or non-ionic surfactants, water-miscible solvents such as methanol, ethanol, propanol, and the like, other thermosetting resins and materials such as urea, melamine, urea-formaldehyde resins, melamine-formaldehyde resins, urea-melamine-formaldehyde resins, phenol-formaldehyde resins, phenol-resorcinol-formaldehyde resins, and a variety of fillers such as wood floor, glass fiber, calcium carbonate, talc, celite, and the like, and a variety of pigments for coloring the cured resin materials. The aqueous resin compositions of the present invention may be dried at low temperatures, such as by spray-drying, and the solid resins powdered or granulated with or without fillers may be used as injection or compression molding.

Use of Diethylene Tricarbamide as Partial Replacement of Urea in Common Urea-Formaldehyde Resins Since diethylene tricarbamide of the present invention reacts with formaldehyde very similarly as urea, it can be incorporated in urea-formaldehyde (UF) resins in various ways, partially replacing the urea component. UF resins are well-known for various wood and other binder uses and their preparation method is also well-known (M. G. Kim and L. W. Amos, *Industrial & Engineering Research*, 29, 208 (1990)). In this well-known process, the first urea ($U_1$) and formaldehyde (F) are reacted at an $F/U_1$ mole ratio of between 1.8 and 2.4 under a weakly alkaline pH and at 90° C.~100° C. for about 30 min. Then, the reaction mixture is acidified to weakly acidic pH and reacted until the target polymerization extent is reached, followed by adjusting the pH back to a weakly alkaline side. After cooling the reaction mixture to about 60° C., the second urea ($U_2$) is added and mixed and the finished resin is cooled to room temperature. The final F/(U+U) mole ratio depends on the amount of second urea, commonly reaching about 1.15 for particleboard binder applications. Thus, in this generally known procedure, diethylene tricarbamide can be used to partially replace first urea, second urea, or both. Such resins can be made with up to 50% replacement of total urea by diethylene tricarbamide and still have good handling characteristics and bonding performance.

Testing and Evaluation Methods of Diethylene Tricarbamide-Formaldehyde (DTC-F) Resins and Other Similar Thermosetting Resins Using DMA Dynamic mechanical analyzer (DMA) is a method widely used to measure and evaluate the curing process of thermosetting resins and their cured products (Lofthouse, M. G. and P. Burroughs, *Journal Thermal Analysis* 13, 439-453 (1978)). This method was used in the present invention using a DMA 983 from TA Instruments. In this procedure, a given amount of resin is impregnated into a piece of glass cloth (1.25 mm wide×18.5 mm long×0.15 mm thick) and the resin-impregnated glass cloth is clamped between the two arms of the instrument. When the test is started, the two arms are periodically flexing and the sample chamber heated according to a predetermined schedule. The sample's rigidity (shear modulus or strength) arising from thermosetting curing of resin is monitored. In this test, the chamber is heated from room temperature at a rate of 25° C. per min to a curing temperature of 160° C. and then maintained at the final temperature (isothermal curing) for about 25 min. The resin-impregnated glass cloth starts from near zero strength (shear modulus) and reaches to the maximum strength after curing. The maximum strength attained often degrades to a lower value due to heat-degradation for some resins in the later part of the test run, reflecting the (in)stability of the cured polymer backbone structures. In this measurement, after the sample is cured, the sample thickness value of cured resin sample is measured manually and incorporated into calculating the actual shear modulus values based on the final sample dimensions to compensate for small differences in resin weights loaded on samples. The maximum strength and cure time values and the stability of the cured resin obtained from DMA measurements, although they are relative (not absolute) values, allowed differentiation among different resins in curing performance. The maximum strength (rigidity) values and cure times from this test are especially useful for comparing the soundness of cured polymer structures or the relative ranking of cross-link density values. Overall, all DMA data obtained amply demonstrated that resins of the present invention are truly thermosetting resins, agreeing with the chemical principles uncovered through resin synthesis and $^{13}$C NMR analysis results.

Figure 2:
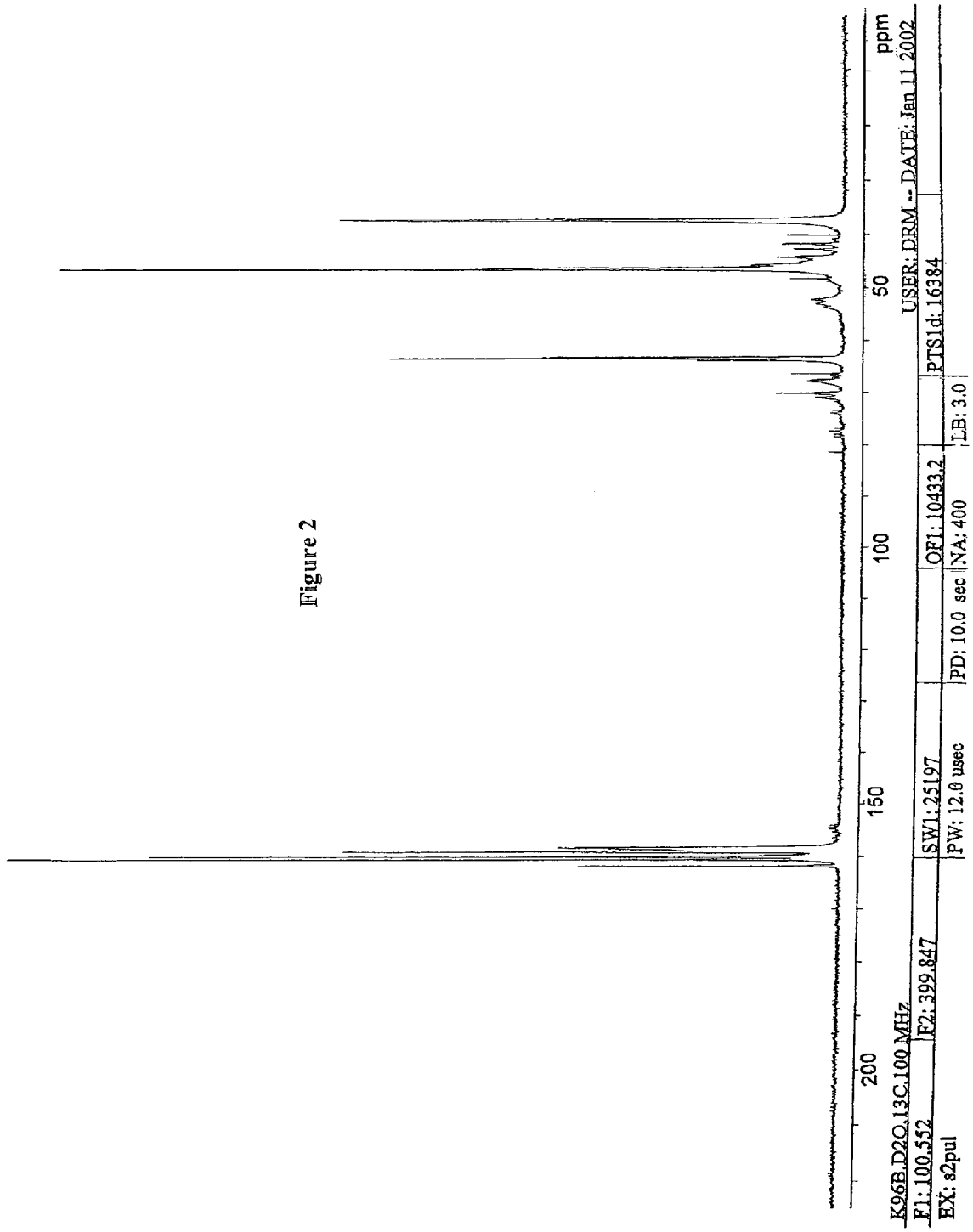
FIG. 2 is a graphical illustration of a typical $^{13}$C NMR spectrum obtained in water for "diethylene tricarbamide-formaldehyde resin" synthesized in Example 1.

$^{13}$C NMR is an effective method of analyzing carbon chemical polymeric structures of diethylene tricarbamide-formaldehyde and similar resins and copolymers used in the present invention, as shown by the example in FIG. 2. The results of the chemical structure analysis from this method were in full agreement with those expected from the synthesis procedures and those presented in the present invention.

Laboratory board manufacture is another method often used for evaluating thermosetting wood adhesive resins, wherein the manufactured boards are tested for the internal bond strengths, formaldehyde emission values, and other properties. Particleboard is convenient to make in a laboratory, as well as medium density fiber board and hardwood plywood panels. Particleboards were made in the present invention as follows: an amount of wood particles was weighed out to give a board 6 in.×6 in. square and 0.5 in. thick at a board density of 50 pounds per cubic feet; a catalyzed binder resin was sprayed onto the wood particles at resin solids level of 8.0% based on wood weight, and the ingredients were mixed well until a good dispersion of resin was attained; a uniform mat was made in a 6 in.×6 in. square box by dispersing and consolidating the resin-applied wood particles; the mat was transferred into a hot press pre-heated at the desired temperature; the mat was pressed to the target thickness in one min or so and kept closed for 3 min; the press was opened and the board cooled. Press temperature was 350° F. The board was then cut and tested for internal bond (IB) strength values according to the method of ASTM D1043 and for the free formaldehyde contents using the European Standard Perforator Extraction Method (DIN EN 120). Briefly, the formaldehyde test method is widely used as an indicator of all free formaldehyde in boards that will come out into the environment over time. The test method is comprised of extracting free formaldehyde in 100 grams of board samples using boiling toluene and the extracted formaldehyde is transferred into the water layer and its amount is determined by a colorimetric method in which the developed color (strength) due to formaldehyde is compared against those of standard solutions. The formaldehyde value is commonly expressed in units of mg/100 gram wood.

The discussion and the description herein also present specific details to provide a thorough understanding of the present invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

EXAMPLES OF DIETHYLENE TRICARBAMIDE-FORMALDEHYDE RESINS AND CONTROL UREA-FORMALDEHYDE RESIN

Example 1

Diethylene Tricarbamide-Formaldehyde (DTC-F) Resins

One hundred twenty (120.0) grams of 50%-formaldehyde (F) solution (2.0 moles) kept at 60° C. and 100.0 grams of water were charged into a 500 mL reaction flask equipped with a cooling condenser, thermometer, magnetic stirrer, and heating mantle and the pH of the solution was adjusted to 8.5 by adding 8% sodium hydroxide solution. Then, the formaldehyde solution was heated to about 85° C. and 232.0 grams of diethylene tricarbamide (DTC) (1.0 mole) were added in small portions over a period of 20 min. The F/DTC mole ratio reached 2.0. The heating of the reaction mixture was continued to maintain the reaction mixture at 85° C.-93° C. and the reaction mixture became clear after a 10 min period indicating the dissolution of DTC from the reaction with formaldehyde. The reaction was continued for 30 min at the same temperature with the pH of the reaction mixture maintained at 6.0-8.0. A sample taken and analyzed using $^{13}$C NMR spectroscopy indicated the quantitative formation of hydroxymethyl groups bonded to the carbamide groups of DTC molecules. The reaction mixture was then acidified by adding 8% sulfuric acid solution to pH 6.2 and the temperature was maintained at 75° C. for one hour. The viscosity of the reaction mixture began at "A" by the Gardener-Holdt Scale and increased to "R." The polycondensation reaction was ended by adjusting the reaction mixture to pH 8.0 by adding 0.8% sodium hydroxide solution and cooling to room temperature. Drying of a one-gram sample of the DTC-F resin at 125° C. for 2 hours resulted in 0.55 gram of colorless resin solids (55.0% resin solids content). The DTC-F resin was analyzed using $^{13}$C NMR spectroscopy (FIG. 2) which indicated the formation of methylene and methylene-ether bonds as well as hydroxymethyl groups on the carbamide groups of DTC. The DTC-F resin was mixed with 0.5% ammonium sulfate catalyst based on the resin solids weight at room temperature and tested for curing using DMA at 160° C. and the results were:
Cure temperature: 160° C.
Maximum shear modulus (psi): 2700
Cure time (min): 7.0
Heat stability: Good Example 2

Mixing Diethylene Tricarbamide-Formaldehyde (DTC-F) Resins with Urea

As an example to show the utility of adding urea to polycarbamide-formaldehyde resins, a batch of DTC-F resin of Example 1 was made and mixed with 19.8 grams of urea (U), resulting in a resin with F/(DTC+U) mole ratio of 1.50. This resin was then mixed with 0.5% ammonium sulfate catalyst based on the resin solids weight at room temperature and tested for curing using DMA at 160° C. and the results were:
Cure temperature: 160° C.
Maximum shear modulus (psi): 2300
Cure time (min): 7.1
Heat stability: Good Example 3

Mixing Diethylene Tricarbamide-Formaldehyde (DTC-F) Resins with Urea for Particleboard Preparation and Formaldehyde Testing As an example to show the utility of adding urea to polycarbamide-formaldehyde resins, another batch of DTC-F resin of Example 1 was made and mixed with 44.3 grams of urea (U), resulting in a resin with F/(DTC+U) mole ratio of 1.15. This resin was mixed with 0.5% ammonium sulfate catalyst based on the resin solids weight at room temperature and used for particleboard manufacturing and the particleboard was tested for the formaldehyde content and internal bond strengths.

Example 4

A Typical Urea-Formaldehyde (UF) Resin for Comparative Purposes

By using a commercial-grade urea and a 50% formaldehyde solution, a typical UF resin was prepared as follows: 300.0 grams of 50% formaldehyde solution (5.0 moles) were charged into a stirred reactor, the pH adjusted to 8.0 with an 8% sodium hydroxide solution, and the reactor heated to 70° C. Then, 143 grams of urea (first urea) were added over a period of 20 min while the reaction exotherm and heating control were used to raise the temperature to 90 ° C. The reaction temperature was maintained by intermittent cooling and, later, by heating for 30 min. Then, by using 8% sulfuric acid solution the pH was lowered to 5.0-5.1 and, by heating, the temperature raised to 95° C. The reaction mixture was kept under this condition for about 110 min with the viscosity advancing to "T" by the Gardner-Holdt Scale. Then, the pH of the reaction mixture was adjusted using 8% sodium hydroxide solution to 8.0 and cooling applied to reach about 60° C., when 118 grams of urea (second urea) were added and stirred until the resin cooled to room temperature. The resin had a viscosity of "K" by the Gardener-Holdt Scale and solids content of 62.5% with calculated formaldehyde/urea mole ratio of 1.15, typical values of current industrial UF resins used in particleboard manufacturing. This resin was mixed with 0.5% ammonium sulfate catalyst based on the resin solids weight at room temperature and tested for curing using DMA at 160° C. and the results were:

Cure temperature: 160° C.
Maximum shear modulus (psi): 1850
Cure time (min): 7.1
Heat stability: Good The UF resin was also mixed with 0.5% ammonium sulfate catalyst and used for manufacturing laboratory particleboard and the board was tested for internal bond strength and formaldehyde content.

Example 5

Bonding Particleboard Using Various Resins of this Disclosure and a Comparative Urea-Formaldehyde Resin and Testing of Particleboard Laboratory particleboards were manufactured using resins of Examples 3 and 4 described above using common current procedures and parameters used by the particleboard industry as follows: board dimensions of 20"×20" and 0.5" thickness; target board density of 50 pounds per cubic feet; binder resin loading level of 10.0% based on wood weight; press time of 3.5 min including one min press-closing time; and press temperatures of 350° F. The internal bond (IB) strength values were obtained for these boards according to the method described in ASTM D1043 and the formaldehyde content values were determined according to the method described in DIN EN 120, as follows:

| Resin | Example 3 | Example 4 |
|---|---|---|
| Resin acronym | DTC-F + U | UF |
| IB strength (psi) | 120 | 115 |
| Formaldehyde Content | 3.6 mg/100 g board | 13.1 mg/100 g board |

In conclusion, the board making and board test results in this Example have demonstrated that diethylene tricarbamide-formaldehyde resins of the present invention are truly thermosetting resins capable of producing strong structural polymer materials useful in many applications, exemplified in bonding of wood particleboard using current manufacturing processes and also having significantly lower formaldehyde content values in boards in comparison to current urea-formaldehyde resin-bonded board. This disclosure has for the first time described and fully characterized the synthesis procedures and structural identities of diethylene tricarbamide and its formaldehyde reaction products. Moreover, this disclosure shows their usefulness in various applications.

The above is a detailed description of particular embodiments of the present invention. All embodiments disclosed and claimed herein can be easily executed in light of this disclosure. While various embodiments of the present invention have been described above, it should be understood that they have been presented by way of example and not limitation. Those of ordinary skill in the relevant art(s), in light of the present disclosure, should recognize and understand that a wide variety of various and obvious changes, alternatives, variations, and modifications in form and detail of the embodiments disclosed herein can be selected and made therein without departing from the true scope and spirit of the present invention. After reading the above description, it will be apparent to those skilled in the relevant art(s) how to implement the invention in alternative embodiments. Thus, the present invention should not be limited by any of the above-described exemplary embodiments. The invention is described both generically and regarding specific embodiments, while the full scope of the invention is set out in the claims and their equivalents that follow. The disclosure and description presented further explain the invention and are not to be interpreted or inferred as limiting thereof. The claims and specification should not be construed to unduly narrow the complete scope of protection to which the present invention is entitled. The disclosure and appended claims are intended to cover all modifications that may fall within the scope of the claims.

Moreover, the present invention is complex in nature and is generally best practiced by empirically determining the appropriate values of the operating parameters, or by conducting computer simulations, to arrive at best design for a given application. Accordingly, all suitable modifications, combinations, and equivalents should be considered as falling within the spirit and scope of the invention. It should also be understood that the figures are presented for example purposes only.

The purpose of the abstract of the disclosure is to enable the U.S. Patent and Trademark Office, the public in general, and particularly the scientists, engineers, and practitioners in the art who are unfamiliar with patent or legal terms or phraseology, to efficiently determine from a cursory inspection the nature and essence of the technical disclosure of the application. The abstract of the disclosure is therefore not intended in any way to be limiting as to the scope of the present invention.

What is claimed is:

1. A method of manufacturing diethylene tricarbamide comprising the steps of:
    mixing diethylenetriamine, urea, and at least one reaction medium comprised of one or more organic solvents to form a reaction mixture;
    reacting said reaction mixture by heating the reaction mixture, up to between about 105° C. and 180° C., or to the boiling point of the reaction mixture within the indicated temperature range, for a predetermined length of time, to generate an ammonia by-product and removing the ammonia by vaporization or by distillation with a part of the reaction mixture to form a first solution or slurry of diethylene tricarbamide in the organic solvents;

cooling said first solution or slurry of diethylene tricarbamide in the organic solvents to complete the formation of precipitates as crude wet diethylene tricarbamide particles;

collecting the crude wet diethylene tricarbamide particles by filtration;

drying the crude wet diethylene tricarbamide particles resulting in dried diethylene tricarbamide;

optionally purifying the crude wet diethylene tricarbamide particles by dispersing in water, in at least one organic solvent, or in a combination thereof, at a predetermined elevated temperature to form a second solution or slurry, a cooling said second solution or slurry to complete the formation of wet purified diethylene tricarbamide crystals, collecting the wet purified diethylene tricarbamide crystals by filtration, and drying the wet purified diethylene tricarbamide crystals resulting in dried diethylene tricarbamide.

2. The method of claim 1, wherein the reaction medium is at least one organic solvent comprising one or more of pyridine, formamide, dimethyl formamide, dimethyl sulfoxide, n-butanol, n-pentanol, cyclohexanol, ethylene glycol, glycerine, and mixtures thereof.

3. The method of claim 1, wherein the solvent of the purifying step is one or more of water, pyridine, formamide, dimethyl formamide, dimethyl sulfoxide, n-butanol, n-pentanol, cyclohexanol, ethylene glycol, glycerine, any low molecular weight alcohols, and mixtures thereof.

4. A method of manufacturing diethylene tricarbamide, the method comprising:

reacting diethylenetriamine with sodium cyanate (NaOCN) at a predetermined elevated temperature in the presence of an equivalent amount of an acid (HX) and water as a solvent for a predetermined period of time to form a reaction mixture comprising sodium salt (NaX) and diethylene tricarbamide suspended or dissolved in the water solvent;

removing sodium salt of the acid from the reaction mixture;

cooling the reaction mixture to room temperature to form colorless precipitates and continued cooling for an effective period of time until separation of colorless precipitates from the water is completed;

collecting the separated colorless precipitates as crude diethylene tricarbamide; and optionally purifying the crude diethylene tricarbamide by dissolving in water, in at least one solvent, or in a combination thereof, at a predetermined elevated temperature followed by cooling, filtration, and drying.

5. The method of claim 4, wherein the solvent of the purifying step comprises one or more of water, pyridine, formamide, dimethyl formamide, dimethyl sulfoxide, n-butanol, n-pentanol, cyclohexanol, ethylene glycol, glycerine, any low molecular weight alcohols, and mixtures thereof.

6. The method of claim 4, wherein the acid (HX) is an inorganic acid, an organic acid, or a combination thereof.

7. A method of using diethylene tricarbamide to make a thermosetting resin composition comprising a 0.5%-100.0% aqueous dispersion or solids, or combination thereof, the method comprising:

reacting a mixture comprising diethylene tricarbamide and formaldehyde to form a condensate, in which the molar ratio of formaldehyde to diethylene tricarbamide is from about 0.3:1 to about 2.6:1, wherein said condensate is prepared in an aqueous medium by reacting at a pH of about 6.0-10.0 for a predetermined length of time, at a temperature of at least 30° C., wherein the reaction mixture has a resulting viscosity at a resin solids concentration of 60% in water at 25° C. of from 1.0 cP or higher;

cooling the resin composition to room temperature; and optionally adding to the resin composition an alkaline material at any temperature during the cooling period to raise the pH to a value of about 6.0-11.0.

8. A method of using diethylene tricarbamide to make a thermosetting resin composition comprising a 0.5%-100.0% aqueous dispersion or solids, or combination thereof, the method comprising:

reacting a mixture comprising diethylene tricarbamide and formaldehyde to form a condensate, in which the molar ratio of formaldehyde to diethylene tricarbamide is from about 0.3:1 to about 2.6:1, wherein said condensate is prepared in an aqueous medium by reacting at a pH value of about 6.0-10.0, at a temperature of at least 30° C., and wherein the reaction mixture has a resulting viscosity at a resin solids concentration of 60% in water at 25° C. of from 1.0 cP or higher;

adding an alkaline material to the condensate to raise the pH to a value of about 6.0-11.0;

adding urea, melamine, diethylene tricarbamide, or a combination thereof, at a predetermined proportion to the resin condensate, wherein the overall molar ratio of the formaldehyde over the combined amount of diethylene tricarbamide, urea, and melamine used in the resin is within the range of from about 0.3 to about 2.60, and wherein the weight quantity of diethylene tricarbamide is about 55%-99%, of urea is about 1%-45%, and of melamine is about 1%-45%; and cooling the resin composition to room temperature.

9. A method of using diethylene tricarbamide to make a thermosetting resin composition comprising a 0.5%-100.0% aqueous dispersion or solids, or combination thereof, the method comprising:

reacting a mixture comprising diethylene tricarbamide, a predetermined proportion of urea, melamine, or a combination thereof, and formaldehyde to form a condensate, in which the molar ratio of formaldehyde to urea, melamine, or a combination thereof, and diethylene tricarbamide is from about 0.3:1 to about 2.6:1, wherein said condensate is prepared in an aqueous medium by reacting at a pH value of about 6.0-10.0, at a temperature of at least 30° C., and wherein the reaction mixture has a resulting viscosity at a resin solids concentration of 60% in water at 25° C. of from 1.0 cP or higher;

adding an alkaline material to the condensate to raise the pH to a value of about 6.0-11.0;

cooling the condensate to room temperature;

adding additional urea, melamine, diethylene tricarbamide, or a combination thereof at any temperature, in a predetermined proportion to the resin condensate, wherein the overall molar ratio of the formaldehyde over the combined amount of diethylene tricarbamide, urea, and melamine used in the resin is within the range of from about 0.3 to about 2.60, and wherein the weight quantity of diethylene tricarbamide is about 55%-99%, of urea is about 1%-45%, and of melamine is about 1%-45%; and additionally cooling the resin composition, if necessary, to room temperature.

10. A thermosetting resin composition made by the method of any of claims 7-9.

11. A thermosetting resin composition made by the method of any of claims 7-9, wherein the composition is cured by heating the resin composition at about 80° C.-300° C. until the resin composition cures completely.

12. A wood composite product made by dispersing or spreading the resin composition of claim 10, wherein the wood composite product comprises wood elements and the resin-applied wood elements are matted and hot-pressed to cure by heating the resin-applied wood elements at about 80° C. -300° C. until the resin composition cures completely.

13. The wood composite product of claim 12, wherein the product is wood particleboard consisting of any wood species, any particle size, and any density and thickness.

14. The wood composite product of claim 12, wherein the product is wet or dry process medium density fiber board consisting of any wood species, any fiber size, and any density and thickness.

15. The wood composite product of claim 12, wherein the product is hardwood or softwood plywood consisting of any wood species.

16. The thermosetting resin composition of claim 11, wherein the resin composition is cured after adding an acid material in a 0.01% -10.0% level based on the resin solids level and then by heating the resin composition at about 80° C.-300° C. until the resin composition cures completely.

17. The wood composite product of claim 12, wherein the resin composition is cured after adding an acid material in a 0.01% -10.0% level based on the resin solids level and then by heating the resin-applied wood elements at about 80° C.-300° C. until the resin composition cures completely.

* * * * *